United States Patent [19]

Hsu

[11] Patent Number: 4,759,794
[45] Date of Patent: Jul. 26, 1988

[54] SYNERGISTIC HERBICIDE COMBINATIONS AND METHOD OF APPLICATION

[75] Inventor: Joanna K. Hsu, Sunnyvale, Calif.

[73] Assignee: Stauffer Chemical Company, Westport, Conn.

[21] Appl. No.: 31,649

[22] Filed: Mar. 30, 1987

Related U.S. Application Data

[63] Continuation of Ser. No. 814,443, Dec. 30, 1985, abandoned.

[51] Int. Cl.⁴ ............................................. A01N 43/68
[52] U.S. Cl. .......................................... 71/93; 71/103; 71/115; 71/118
[58] Field of Search ................................... 71/93, 103

[56] References Cited

FOREIGN PATENT DOCUMENTS 013963 4/1981 European Pat. Off. .

Primary Examiner—Catherine L. Mills
Attorney, Agent, or Firm—Hana Dolezlova; Paul R. Martin; Edwin H. Baker

[57] ABSTRACT

A synergistic herbicidal composition comprising a mixture of: (a) a herbicidally effective amount of 2-(2-chloro-4-methanesulfonylbenzoyl)-1,3-cyclohexanedione; and (b) a herbicidally effective amount of a compound selected from the group consisting of 2-chloro-4-(ethylamino)-6-(isopropylamino)-s-triazine, 3-amino-2,5-dichlorobenzoic acid, and 2-chloro-N-isopropylacetanilide, and mixtures thereof; at a weight ratio of (a) to (b) of from about 0.1:1 to about 20:1.

12 Claims, No Drawings

SYNERGISTIC HERBICIDE COMBINATIONS AND METHOD OF APPLICATION

This is a continuation of application Ser. No. 814,443, filed Dec. 30, 1985, abandoned.

BACKGROUND OF THE INVENTION

The protection of crops from weeds and other vegetation which inhibit crop growth is a constantly recurring problem in agriculture. To help combat this problem researchers in the field of synthetic chemistry have produced an extensive variety of chemicals and chemical formulations effective in the control of such unwanted growth. Chemical herbicides of many types have been disclosed in the literature and a large number are in commercial use.

In some cases, active herbicides have been shown to be more effective in combination than when applied individually. The result is often termed "synergism" since the combination demonstrates a potency or activity level exceeding that which it would be expected to have, based on a knowledge of the individual potencies of the components. The present invention resides in the discovery that certain cyclohexanediones and other chemical compounds already known individually for their herbicidal potency, display this synergism when applied in combination.

THE PRIOR ART

The compounds which can be combined to form the synergistic herbicidal compositions of this invention are already known in the art as herbicides. One such compound is 2-(2-chloro-4-methanesulfonylbenzoy)-1,3-cyclohexanedione. This compound is disclosed in European Patent Publication No. 137,963, published 4-4-85. It is also disclosed and claimed in U.S. application Ser. No. 634,408. Another of the compounds used in the synergistic compositions of the invention is 2-chloro-4-(ethylamino)-6-(isopropylamino)-striazine, commonly know as Atrazine. Still another compound used in the synergistic hericidal composition of this invention is 3-amino-2,5-dichlorobenzoic acid, commonly known as Chloramben, described and claimed in U.S. Pat. Nos. 3,014,063 and 3,174,842. Yet another compound used in the synergistic compositions of this invention is 2-chloro-4-N-isopropylacetanilide, commonly known as Propachor.

DESCRIPTION OF THE INVENTION

It has now been discovered that synergism in the control of undesirable vegetation is exhibited by compositions comprising a mixture of the following components:

(a) a herbicidally effective amount of 2-(2-chloro-4-methanesulfonylbenzoyl)-1,3-cyclohexandione; and (b) a herbicidally effective amount of a compound selected from the group consisting of 3-(amino-2,5-dichlorobenzoic acid, 2-chloro-N-isopropylacetanilide or 2-chloro-4-(ethylamino)-6-(isopropylamino)-s-triazine, and mixtures thereof.

Another embodiment of this invention is a method of controlling undesirable weed pests, and this method comprises applying the synergistic compositions of the invention to the locus where control is desired.

The terms "synergism" and "synergistic" are used herein to convey the result observed when a combination of herbicides demonstrates a potency in excess of that which the combination would be expected to produce on the basis of the potencies of each herbicide applied individually.

The term "herbicide" is used herein to denote a compound which controls or modifies the growth of plants. The term "herbicidally effective amount" is used to indicate the quantity of such a compound or combination of such compounds which is capable of producing a controlling or modifying effect. Controlling or modifying effects include all deviations from natural development, for example: killing, retardation, leaf burn, dwarfing and the like. The term "plants" is used to include all postemergent vegetation, ranging from seedlings to established vegetation.

As previously mentioned, the synergistic compositions of this invention all employ chemical compounds previously known for their herbicidal activity. One of these compounds, 2-(2-chloro-4-methanesulfonylbenzoyl)-1,3-cyclohexanedione, is disclosed in European Patent Application No. 0 137 963, published 4-4-85, and it is also disclosed and claimed in U.S. application Ser. No. 634,408. Still another compound 2-chloro-4-(ethylamino)-6-(isopropylamino)-s-triazine, commonly known as Atrazine, is commercially sold under various tradenames, and is described in the *Herbicide Handbook of the Weed Science Society of America*, 5th Edition, 1983. Another of the compounds used in the synergistic combinations of the invention, 3-amino-2,5-dichlorobenzoic acid, is commercially available under a number of tradenames and is described on page 92 of the *Herbicide Handbook of the Weed Science Society of America*, 5Edition, 1983. Yet another compound used in the synergistic compositions of this invention is 2-chloro-4-N-isopropylacetanilide, is described on pages 401 and 402 of the *Herbicide Handbook of the Weed Science Society of America*, 5th Edition, 1983.

These compounds are effectively used in the synergistic compositions of the invention at ratios of Compound (a) to Compound (b) as set forth above, ranging from about 0.01:1 to about 20:1. Preferably, the ratio of Compound (a) to Compound (b) is from about 0.1:1 to about 10:1.

HERBICIDAL TEST DATA

Synergism for the compositions of this invention was measured in accordance with the following test:

Aluminum pans measuring 9×6×4 inches (cm) were filled with a sandy loam soil and 6 furrows were impressed across the width of each flat. A number of weed species were seeded into furrows and covered with soil. Along with the seed species were two corn hybrids which were inserted to determine the extend of damage, if any, upon plant species.

The weed species were as follows:

| Abbreviation | Common Name | Scientific Name |
| --- | --- | --- |
| YNS | yellow nutsedge | *Cyperus esculentus* |
| PNS | purple nutsedge | *Cyperus rotundus* |
| RJG | rhizome johnsongrass | *Sorghum halepense* |
| FP | fall panicum | *Panicum dichotomiflorum* |
| WPM | wild proso millet | *Panicum milaceum* |
| GG | goosegrass | *Eleusine indica* |
| SC | shattercane | *Sorghum bicolor* |
| YFT | yellow foxtail | *Setaria lutescens* |
| GFT | green foxtail | *Seteria viridis* |
| PW | redroot pigweed | *Amaranthus retroflexus* |
| AMG | annual morninggglory | *Ipomoea purpurea* |
| SP | sicklepod | *Cassia obtusifolia* |
| VL | velvetleaf | *Abutilon theophrasti* |

-continued

| Abbreviation | Common Name | Scientific Name |
|---|---|---|
| LCG | large crabgrass | *Digitaria ischaemum* |
| JG | johnsongrass | *Sorghum halepense* |

The plant species were as follows:

| CN | corn | *Zea maize* (L.) |
|---|---|---|

Chemical solutions, which in the case of pre-emergence testing were sprayed the same day of seeding, were prepared as follows:

All compounds were of technical grade, except Prowl which was what is termed a 4E formulation, which means a 4 pound per gallon emulsion concentrate. All of the technical grade compounds were either applied singly, or applied in conjunction with the synergistic herbicidal compound, by diluting the technical grade compounds with acetone and water at 1:1 ratio water and applying at a spray volume of 25 gal/acre. The quantity of active ingredient for each compounds which was applied is indicated under the heading "Application Rate".

In the case of post-emergent testing, the weed and plant species were allowed to sprout and application was made approximately 2 weeks after planting.

The various rates of application are indicated in the tables under "Application Rate".

Flats were then placed in a greenhouse, and watered by overhead sprinkling. Air temperatures ranged from 18° C. to 27° C. Flats were kept moist during the course of each experiment.

After treatment, each row of seedlings was visually rated for growth control due to all factors of injury. In pre-emergence testing the ratings were done 28 days after treatment. In post-emergent testing, the rating was done 21 days after treatment. Untreated flats of seedlings were used for comparison, zero percent injury of growth control is equivalent to growth in control flats. One hundred percent growth control is equivalent to complete kill.

Herbicide interaction responses were evaluated by use of Limpel's formula (Limpel, L. E., et al., 1962, "Weed Control by Dimethyltetrachloroterephthalate Alone and in Certain Combinations," *Proc. NEWCC*, 16:48–53):

$$E = X + Y - \frac{XY}{100}$$

where
E = expected response
where
X = observed (O) value or percent growth control when the herbicide is applied singly; and
Y = observed (O) value or percent growth control when the second herbicide is applied singly.

A response is synergistic when an observed value is greater than the calculated value, a synergistic response is understood to be one in which the interaction response is greater than the sum of responses from the individual chemical treatments. An antagonistic response is the opposite situation.

In the tables which follows:
E = expected activity
O = observed activity
R = result, i.e., additive (AD), antagonistic (A) or synergistic (S)

TABLE 1

| Treatment | Application Rate lb/A | Pre-Emergence YNS O | E | R | PNS O | E | R | RJG O | E | R | CN O | E | R | CN O | E | R |
|---|---|---|---|---|---|---|---|---|---|---|---|---|---|---|---|---|
| X-100 | ¼ | 85 | | | 65 | | | 0 | | | 0 | | | 0 | | |
|  | ½ | 90 | | | 95 | | | 30 | | | 0 | | | 0 | | |
| ATRAZINE | ¼ | 0 | | | 0 | | | 0 | | | 0 | | | 0 | | |
|  | ½ | 0 | | | 0 | | | 0 | | | 0 | | | 0 | | |
| LASSO | ½ | 100 | | | 80 | | | 0 | | | 0 | | | 0 | | |
|  | 1 | 100 | | | 100 | | | 0 | | | 0 | | | 0 | | |
| AMIBEN | 1 | 0 | | | 0 | | | 30 | | | 0 | | | 15 | | |
|  | 2 | 0 | | | 65 | | | 50 | | | 70 | | | 25 | | |
| PROWL | ¼ | 0 | | | 0 | | | 20 | | | 0 | | | 0 | | |
|  | ½ | 0 | | | 0 | | | 0 | | | 50 | | | 10 | | |
| RAMROD | 2 | 20 | | | 30 | | | 0 | | | 0 | | | 0 | | |
|  | 3 | 100 | | | 90 | | | 0 | | | 0 | | | 0 | | |
| X-100 | ¼ + ¼ | 90 | 85 | S | 80 | 65 | S | 20 | 0 | S | 0 | 0 | | 0 | 0 | |
| + | ½ + ¼ | 95 | 90 | S | 90 | 95 | A | 30 | 30 | AD | 0 | 0 | | 0 | 0 | |
| ATRAZINE | ¼ + ½ | 98 | 95 | S | 95 | 65 | S | 20 | 0 | S | 0 | 0 | | 0 | 0 | |
|  | ½ + ½ | 95 | 90 | S | 95 | 95 | AD | 30 | 30 | AD | 0 | 0 | | 0 | 0 | |
| X-100 | ¼ + ½ | 100 | 100 | AD | 95 | 93 | S | 15 | 0 | S | 0 | 0 | | 0 | 0 | |
| + | ½ + ½ | 98 | 100 | A | 85 | 99 | A | 40 | 30 | S | 0 | 0 | | 0 | 0 | |
| LASSO | ¼ + 1 | 95 | 100 | A | 95 | 100 | A | 20 | 0 | S | 0 | 0 | | 0 | 0 | |
|  | ½ + 1 | 95 | 100 | A | 100 | 100 | AD | 60 | 30 | S | 10 | 0 | | 10 | 0 | |
| X-100 | ¼ + 1 | 95 | 85 | S | 95 | 65 | S | 20 | 30 | A | 0 | 0 | | 30 | 15 | |
| + | ½ + 1 | 98 | 90 | S | 98 | 95 | S | 50 | 51 | A | 40 | 0 | | 30 | 15 | |
| AMIBEN | ¼ + 2 | 95 | 85 | S | 95 | 88 | S | 30 | 50 | A | 25 | 70 | | 40 | 25 | |
|  | ½ + 2 | 95 | 90 | S | 98 | 98 | AD | 75 | 65 | S | 65 | 70 | | 50 | 25 | |
| X-100 | ¼ + ¼ | 95 | 85 | S | 95 | 65 | S | 10 | 20 | A | 20 | 0 | | 0 | 0 | |
| + | ½ + ¼ | 95 | 90 | S | 98 | 95 | S | 55 | 44 | S | 25 | 0 | | 30 | 0 | |
| PROWL | ¼ + ½ | 95 | 90 | S | 95 | 95 | AD | 10 | 0 | S | 40 | 50 | | 20 | 10 | |
|  | ½ + ½ | 95 | 90 | S | 95 | 95 | AD | 10 | 30 | A | 45 | 50 | | 40 | 10 | |
| X-100 | ¼ + 2 | 95 | 88 | S | 98 | 76 | S | 5 | 0 | S | 0 | 0 | | 0 | 0 | |
| + | ½ + 2 | 95 | 92 | S | 99 | 97 | S | 15 | 30 | A | 0 | 0 | | 0 | 0 | |
| RAMROD | ¼ + 3 | 100 | 100 | AD | 100 | 97 | S | 5 | 0 | S | 0 | 0 | | 0 | 0 | |
|  | ½ + 3 | 95 | 100 | A | 95 | 100 | A | 65 | 30 | S | 0 | 0 | | 0 | 0 | |

TABLE 1-continued

| Application | | Pre-Emergence | | | | | | | | | | | | | |
|---|---|---|---|---|---|---|---|---|---|---|---|---|---|---|---|
| | | YNS | | | PNS | | | RJG | | | CN | | | CN | |
| Treatment | Rate lb/A | O | E | R | O | E | R | O | E | R | O | E | R | O | E | R |
| CONTROL | — | 0 | 0 | 0 | 0 | 0 | 0 | 0 | 0 | 0 | 0 | 0 | 0 | 0 | 0 | |

X-100 = 2-(2-chloro-4-methanesulfonylbenzoyl)-1,3-cyclohexanedione
Atrazine = 2-chloro-4-(ethylamino)-6-isopropylamino)-s-triazine
Lasso = 2-chloro-2',6'-diethyl-N—(methoxymethyl)acetanilide
Amiben = 3-amino-2,5-dichlorobenzoic acid
Prowl = N—(1-ethylpropyl)-3,4-dimethyl-2,6-dinitrobenzeneamine
Ramrod = 2-chloro-N—isopropylacetanilide

TABLE 2

Pre-Emergence

| Treatment | Rate lb/A | FP O | E | R | WPM O | E | R | GG O | E | R | SC O | E | R | YFT O | E | R | GFT O | E | R |
|---|---|---|---|---|---|---|---|---|---|---|---|---|---|---|---|---|---|---|---|
| X-100 | ¼ | 20 | | | 95 | | | 100 | | | 15 | | | 95 | | | 10 | | |
| | ½ | 100 | | | 100 | | | 100 | | | 95 | | | 90 | | | 65 | | |
| ATRA- | ¼ | 60 | | | 0 | | | 65 | | | 0 | | | 45 | | | 30 | | |
| ZINE | ½ | 70 | | | 40 | | | 95 | | | 0 | | | 80 | | | 60 | | |
| LASSO | ½ | 100 | | | 95 | | | 100 | | | 90 | | | 90 | | | 100 | | |
| | 1 | 100 | | | 98 | | | 100 | | | 100 | | | 90 | | | 100 | | |
| AMIBEN | 1 | 100 | | | 95 | | | 95 | | | 0 | | | 75 | | | 45 | | |
| | 2 | 95 | | | 95 | | | 100 | | | 0 | | | 85 | | | 85 | | |
| PROWL | ¼ | 100 | | | 95 | | | 100 | | | 90 | | | 95 | | | 95 | | |
| | ½ | 100 | | | 100 | | | 100 | | | 100 | | | 100 | | | 100 | | |
| RAMROD | 2 | 75 | | | 50 | | | 95 | | | 0 | | | 90 | | | 95 | | |
| | 3 | 100 | | | 90 | | | 100 | | | 0 | | | 98 | | | 100 | | |
| X-100 | ¼+¼ | 100 | 68 | S | 100 | 95 | S | 100 | 100 | AD | 100 | 15 | S | 90 | 97 | A | 100 | 37. | S |
| + | ½+¼ | 100 | 100 | AD | 100 | 100 | AD | 100 | 100 | AD | 95 | 95 | AD | 95 | 94 | S | 100 | 75 | S |
| ATRA- | ¼+½ | 95 | 75 | S | 100 | 97 | S | 100 | 100 | AD | 90 | 15 | S | 90 | 99 | A | 100 | 64 | S |
| ZINE | ½+½ | 100 | 100 | AD | 100 | 100 | AD | 100 | 100 | AD | 100 | 95 | S | 100 | 98 | S | 100 | 86 | S |
| X-100 | ¼+½ | 100 | 100 | AD | 100 | 100 | AD | 100 | 100 | AD | 90 | 91 | A | 85 | 99 | A | 100 | 100 | AD |
| + | ½+½ | 100 | 100 | AD | 100 | 100 | AD | 100 | 100 | AD | 98 | 93 | A | 100 | 99 | S | 100 | 100 | AD |
| LASSO | ¼+1 | 100 | 100 | AD | 100 | 100 | AD | 100 | 100 | AD | 95 | 100 | A | 100 | 99 | A | 100 | 100 | AD |
| | ½+1 | 100 | 100 | AD | 100 | 100 | AD | 100 | 100 | AD | 98 | 100 | A | 100 | 99 | S | 100 | 100 | AD |
| X-100 | ¼+1 | 100 | 100 | AD | 100 | 100 | AD | 100 | 100 | AD | 100 | 15 | S | 98 | 99 | A | 100 | 50 | S |
| + | ½+1 | 100 | 100 | AD | 100 | 100 | AD | 100 | 100 | AD | 98 | 95 | S | 98 | 98 | AD | 100 | 81 | S |
| AMIBEN | ¼+2 | 100 | 96 | S | 100 | 100 | AD | 100 | 100 | AD | 70 | 15 | S | 80 | 99 | A | 100 | 86 | S |
| | ½+2 | 100 | 100 | AD | 100 | 100 | AD | 100 | 100 | AD | 98 | 95 | S | 95 | 98 | A | 95 | 95 | AD |
| X-100 | ¼+¼ | 100 | 100 | AD | 98 | 100 | A | 100 | 100 | AD | 95 | 91 | S | 100 | 100 | AD | 100 | 95 | S |
| + | ½+¼ | 100 | 100 | AD | 100 | 100 | AD | 100 | 100 | AD | 98 | 99 | A | 100 | 99 | S | 100 | 98 | S |
| PROWL | ¼+½ | 100 | 100 | AD | 100 | 100 | AD | 100 | 100 | AD | 98 | 100 | A | 100 | 100 | AD | 100 | 100 | AD |
| | ½+½ | 100 | 100 | AD | 100 | 100 | AD | 100 | 100 | AD | 100 | 100 | AD | 100 | 100 | AD | 100 | 100 | AD |
| X-100 | ¼+2 | 100 | 80 | S | 100 | 97 | A | 100 | 100 | AD | 90 | 15 | S | 100 | 99 | S | 100 | 95 | S |
| + | ½+2 | 100 | 100 | AD | 100 | 100 | AD | 100 | 100 | AD | 100 | 95 | S | 100 | 99 | S | 100 | 98 | S |
| RAMROD | ¼+3 | 100 | 100 | AD | 100 | 100 | AD | 100 | 100 | AD | 65 | 15 | S | 100 | 100 | AD | 100 | 100 | AD |
| | ½+3 | 100 | 100 | AD | 100 | 100 | AD | 100 | 100 | AD | 85 | 95 | A | 100 | 100 | AD | 100 | 100 | AD |
| CON-TROL | — | 0 | 0 | 0 | 0 | 0 | 0 | 0 | 0 | 0 | 0 | 0 | 0 | 0 | 0 | | | | |

TABLE 3

Pre-Emergence

| Treatment | Rate lb/A | PW O | E | R | AMG O | E | R | SP O | E | R | VL O | E | R | LCG O | E | R | JG O | E | R |
|---|---|---|---|---|---|---|---|---|---|---|---|---|---|---|---|---|---|---|---|
| X-100 | ¼ | 100 | | | 100 | | | 20 | | | 100 | | | 75 | | | 20 | | |
| | ½ | 70 | | | 100 | | | 70 | | | 100 | | | 100 | | | 95 | | |
| ATRAZINE | ¼ | 100 | | | 100 | | | 0 | | | 100 | | | 10 | | | 0 | | |
| | ½ | 100 | | | 100 | | | 55 | | | 100 | | | 10 | | | 45 | | |
| LASSO | ½ | 90 | | | 0 | | | 60 | | | 65 | | | 90 | | | 100 | | |
| | 1 | 95 | | | 10 | | | 85 | | | 60 | | | 100 | | | 100 | | |
| AMIBEN | 1 | 40 | | | 0 | | | 50 | | | 100 | | | 90 | | | 95 | | |
| | 2 | 80 | | | 0 | | | 65 | | | 100 | | | 90 | | | 98 | | |
| PROWL | ¼ | 70 | | | 0 | | | 0 | | | 0 | | | 80 | | | 80 | | |
| | ½ | 85 | | | 0 | | | 0 | | | 85 | | | 100 | | | 95 | | |
| RAMROD | 2 | 60 | | | 0 | | | 0 | | | 0 | | | 50 | | | 75 | | |
| | 3 | 100 | | | 10 | | | 60 | | | 30 | | | 85 | | | 95 | | |
| X-100 | ¼ + ¼ | 100 | 100 | AD | 100 | 100 | AD | 60 | 20 | S | 100 | 100 | AD | 100 | 77 | S | 85 | 20 | S |
| + | ½ + ¼ | 100 | 100 | AD | 100 | 100 | AD | 90 | 70 | S | 100 | 100 | AD | 100 | 100 | AD | 95 | 95 | AD |
| ATRAZINE | ¼ + ½ | 100 | 100 | AD | 100 | 100 | AD | 98 | 64 | S | 100 | 100 | AD | 100 | 77 | S | 95 | 56 | S |
| | ½ + ½ | 100 | 100 | AD | 100 | 100 | AD | 95 | 86 | S | 100 | 100 | AD | 100 | 100 | AD | 100 | 97 | S |
| X-100 | ¼ + ½ | 100 | 100 | AD | 100 | 100 | AD | 85 | 68 | S | 100 | 100 | AD | 100 | 97 | S | 100 | 100 | AD |
| + | ½ + ½ | 100 | 97 | S | 100 | 100 | AD | 100 | 88 | S | 100 | 100 | AD | 100 | 100 | AD | 100 | 100 | AD |
| LASSO | ¼ + 1 | 100 | 100 | AD | 100 | 100 | AD | 98 | 88 | S | 100 | 100 | AD | 100 | 100 | AD | 100 | 100 | AD |
| | ½ + 1 | 100 | 98 | S | 100 | 100 | AD | 98 | 95 | S | 100 | 100 | AD | 100 | 100 | AD | 100 | 100 | AD |

TABLE 3-continued

Pre-Emergence

| Treatment | Application Rate lb/A | PW O | PW E | PW R | AMG O | AMG E | AMG R | SP O | SP E | SP R | VL O | VL E | VL R | LCG O | LCG E | LCG R | JG O | JG E | JG R |
|---|---|---|---|---|---|---|---|---|---|---|---|---|---|---|---|---|---|---|---|
| X-100 | ¼ + 1 | 98 | 100 | A | 100 | 100 | AD | 90 | 60 | S | 100 | 100 | AD | 100 | 97 | S | 100 | 96 | S |
| + | ½ + 1 | 100 | 82 | S | 100 | 100 | AD | 98 | 95 | S | 100 | 100 | AD | 100 | 100 | AD | 98 | 99 | A |
| AMIBEN | ¼ + 2 | 100 | 100 | AD | 100 | 100 | AD | 80 | 72 | S | 100 | 100 | AD | 100 | 97 | S | 100 | 98 | S |
| | ½ + 2 | 100 | 94 | S | 100 | 100 | AD | 85 | 89 | A | 100 | 100 | AD | 100 | 100 | AD | 100 | 99 | S |
| X-100 | ¼ + ¼ | 100 | 100 | AD | 100 | 100 | AD | 60 | 20 | S | 100 | 100 | AD | 100 | 95 | S | 95 | 84 | S |
| + | ½ + ¼ | 100 | 91 | S | 100 | 100 | AD | 85 | 70 | S | 100 | 100 | AD | 100 | 100 | AD | 100 | 99 | S |
| PROWL | ¼ + ½ | 100 | 100 | AD | 95 | 100 | A | 40 | 20 | S | 100 | 100 | AD | 100 | 100 | AD | 100 | 96 | S |
| | ½ + ½ | 100 | 95 | S | 98 | 100 | A | 75 | 70 | S | 100 | 100 | AD | 100 | 100 | AD | 100 | 99 | S |
| X-100 | ¼ + 2 | 100 | 100 | AD | 100 | 100 | AD | 100 | 20 | S | 100 | 100 | AD | 100 | 87 | S | 65 | 80 | A |
| + | ½ + 2 | 100 | 88 | S | 100 | 100 | AD | 90 | 70 | S | 100 | 100 | AD | 100 | 100 | AD | 80 | 96 | A |
| RAMROD | ¼ + 3 | 100 | 100 | AD | 100 | 100 | AD | 85 | 68 | S | 100 | 100 | AD | 100 | 96 | S | 80 | 96 | A |
| | ½ + 3 | 100 | 100 | AD | 100 | 100 | AD | 90 | 88 | S | 100 | 100 | AD | 100 | 100 | AD | 95 | 99 | A |
| CONTROL | — | 0 | 0 | | 0 | 0 | | 0 | 0 | | 0 | 0 | | 0 | 0 | | 0 | 0 | |

TABLE 4

Post-Emergence

| Treatment | Application Rate lb/A | PW O | PW E | PW R | CB O | CB E | CB R | AMG O | AMG E | AMG R | SP O | SP E | SP R | VL O | VL E | VL R | YNS O | YNS E | YNS R |
|---|---|---|---|---|---|---|---|---|---|---|---|---|---|---|---|---|---|---|---|
| X-100 | ¼ | 70 | | | 80 | | | 75 | | | 20 | | | 100 | | | 80 | | |
| | ½ | 65 | | | 95 | | | 100 | | | 50 | | | 100 | | | 90 | | |
| ATRAZINE | ¼ | 100 | | | 100 | | | 100 | | | 40 | | | 100 | | | 20 | | |
| | ½ | 100 | | | 100 | | | 100 | | | 60 | | | 100 | | | 35 | | |
| X-100 | ¼ + ¼ | 100 | 100 | AD | 100 | 100 | AD | 100 | 100 | AD | 55 | 52 | S | 100 | 100 | AD | 80 | 84 | A |
| + | ½ + ¼ | 100 | 100 | AD | 100 | 100 | AD | 100 | 100 | AD | 70 | 70 | AD | 100 | 100 | AD | 95 | 92 | S |
| ATRAZINE | ¼ + ½ | 100 | 100 | AD | 100 | 100 | AD | 100 | 100 | AD | 90 | 68 | S | 100 | 100 | AD | 90 | 87 | A |
| | ½ + ½ | 100 | 100 | AD | 100 | 100 | AD | 100 | 100 | AD | 100 | 80 | S | 100 | 100 | AD | 90 | 94 | A |
| CONTROL | — | 0 | 0 | | 0 | 0 | | 0 | 0 | | 0 | 0 | | 0 | 0 | | 0 | 0 | |

TABLE 5

Post-Emergence

| Treatment | Application Rate lb/A | LCG O | LCG E | LCG R | JG O | JG E | JG R | WPM O | WPM E | WPM R | FP O | FP E | FP R | GG O | GG E | GG R | SC O | SC E | SC R |
|---|---|---|---|---|---|---|---|---|---|---|---|---|---|---|---|---|---|---|---|
| X-100 | ¼ | 100 | | | 100 | | | 95 | | | 75 | | | 70 | | | 45 | | |
| | ½ | 100 | | | 100 | | | 90 | | | 80 | | | 80 | | | 60 | | |
| ATRAZINE | ¼ | 85 | | | 25 | | | 35 | | | 20 | | | 65 | | | 20 | | |
| | ½ | 75 | | | 20 | | | 35 | | | 40 | | | 60 | | | 10 | | |
| X-100 | ¼ + ¼ | 100 | 100 | AD | 95 | 100 | A | 95 | 97 | A | 80 | 80 | AD | 70 | 90 | A | 25 | 56 | A |
| + | ½ + ¼ | 100 | 100 | AD | 100 | 100 | AD | 100 | 94 | S | 60 | 84 | A | 90 | 93 | A | 60 | 68 | S |
| ATRAZINE | ¼ + ½ | 100 | 100 | AD | 90 | 100 | A | 100 | 97 | S | 100 | 85 | S | 100 | 88 | S | 35 | 51 | A |
| | ½ + ½ | 100 | 100 | AD | 100 | 100 | AD | 100 | 94 | S | 75 | 88 | A | 100 | 92 | S | 40 | 64 | A |
| CONTROL | — | 0 | 0 | | 0 | 0 | | 0 | 0 | | 0 | 0 | | 0 | 0 | | 0 | 0 | |

TABLE 6

Post-Emergence

| Treatment | Application Rate lb/A | SA O | SA E | SA R | RJG O | RJG E | RJG R | YFT O | YFT E | YFT R | GFT O | GFT E | GFT R | CORN 55A O | CORN 55A E | CORN 55A R | CORN 23A O | CORN 23A E | CORN 23A R |
|---|---|---|---|---|---|---|---|---|---|---|---|---|---|---|---|---|---|---|---|
| X-100 | ¼ | 80 | | | 0 | | | 75 | | | 75 | | | 0 | | | 0 | | |
| | ½ | 90 | | | 20 | | | 85 | | | 90 | | | 0 | | | 0 | | |
| ATRAZINE | ¼ | 100 | | | 0 | | | 65 | | | 70 | | | 0 | | | 0 | | |
| | ½ | 95 | | | 0 | | | 65 | | | 75 | | | 0 | | | 0 | | |
| X-100 | ¼ + ¼ | 100 | 100 | AD | 0 | 0 | AD | 75 | 91 | A | 70 | 93 | A | 0 | 0 | | 0 | 0 | |
| + | ½ + ¼ | 95 | 100 | A | 10 | 20 | A | 100 | 95 | S | 100 | 97 | S | 0 | 0 | | 0 | 0 | |
| ATRAZINE | ¼ + ½ | 100 | 99 | S | 10 | 0 | S | 100 | 91 | S | 98 | 94 | S | 0 | 0 | | 0 | 0 | |
| | ½ + ½ | 100 | 100 | AD | 0 | 20 | A | 98 | 95 | A | 95 | 98 | A | 0 | 0 | | 0 | 0 | |
| CONTROL | — | 0 | 0 | | 0 | 0 | | 0 | 0 | | 0 | 0 | | 0 | 0 | | 0 | 0 | |

Application rates for the compositions of this invention will depend upon the weeds to be controlled and the degree of control desired. In general, the compositions of this invention are most efficiently employed at a rate of 0.01 to 50 pounds per acre (0.011 to 56 kilograms per hectare) of the active ingredients, preferably 0.1 to 25 pounds per acre (0.11 to 28 kilograms per hectare).

The compositions of the present invention show synergistic activity as herbicides in controlling the growth of undesirable vegetation when applied to such vegetation in pre- or postemergence application. The compositions are generally embodied in formulations which contain inert or occasionally active ingredients or diluent carriers in addition to the active compounds. Examples of such ingredients or carriers are water, organic solvents, surface active agents, oil, water-in-oil emulsions, wetting agents, dispersing agents, and emulsifying agents. The herbicidal formulations generally take the form of wettable powders, solutions or emulsifiable concentrates.

Wettable powders are finely divided compositions comprising a particulate carrier impregnated with the herbicidal compound and additionally containing one or more surface active agents. The surface active agent promotes rapid dispersion of the powder in aqueous medium to form stable, sprayable suspensions. A wide variety of surface active agents can be used, for example, long chain fatty alcohols and alkali metal salts of the sulfates fatty alcohols, salts of sulfonic acid; esters of long chain fatty acids; and polyhydric alcohols, in which the alcohol groups are free, omega-substituted polyethylene glycols of relatively long chain length.

The herbicidal compositions can also be applied to the foilage in the form of a solution in a suitable solvent. Solvents frequently used in herbicidal formulations include kerosene, fuel oil, xylene, petroleum fractions with boiling ranges above xylene, and aromatic petroleum fractions rich in methylated naphthalenes.

The most preferred formulations are emulsifiable concentrations which consist of an oil solution of the herbicide along with an emulsifying agent. Prior to use the concentrate is diluted with water to form a suspended emulsion of oil droplets. The emulsifiers used are usually a mixture of anionic and nonionic surfactants. Other additives such as spreading agents and stickers can be included in the emulsifiable concentrate.

The formulations described above can be applied to the vegetation sought to be controlled in any conventional manner either before or after the vegetation has emerged from the soil. The vegetation can be in any stage of development after emergence, ranging from seedlings to fully grown plants. Application can be achieved by any conventional technique such as the use of ground spraying equipment or aircraft-mounted sprayers. Various other application techniques will be apparent to one skilled in the pesticide art.

What is claimed is:

1. A synergistic herbicidal composition comprising a mixture of:
    (a) a herbicidally effective amount of 2-(2-chloro-4-methanesulfonylbenzoyl)-1,3-cyclohexanedione; and
    (b) a herbicidally effective amount of a compound selected from the group consisting of 2-chloro-4-(ethylamino)-6-(isopropylamino)-s-triazine, 3-amino-2,5-dichlorobenzoic acid, and 2-chloro-N-isopropylacetanilide, and mixtures thereof;
    at a weight ratio of (a) to (b) of from about 1:2 to about 2:1.

2. The composition of claim 1 wherein (b) is 2-chloro-4-(ethylamino)-6-(isopropylamino)-s-triazine.

3. The composition of claim 1 wherein (b) is 3-amino-2,5-dichlorobenzoic acid.

4. The composition of claim 1 wherein (b) is 2-chloro-N-isopropylacetanilide.

5. A synergistic herbicidal composition comprising a mixture of:
    (a) a herbicidally effective amount of 2-(2-chloro-4-methanesulfonylbenzoyl)-1,3-cyclohexanedione;
    (b) a herbicidally effective amount of a compound selected from the group consisting of 2-chloro-4-(ethylamino)-6-(isopropylamino)-s-triazine, 3-amino-2,5-dichlorobenzoic acid, and 2-chloro-N-isopropylacetanilide, and mixtures thereof; and
    (c) an inert diluent carrier, at a weight ratio of (a) to (b) of from about 1:2 to about 2:1.

6. The composition of claim 5 wherein (b) is 2-chloro-4-(ethylamino)-6-(isopropylamino)-s-triazine.

7. The composition of claim 5 wherein (b) is 3-amino-2,5-dichlorobenzoic acid.

8. The composition of claim 5 wherein (b) is 2-chloro-N-isopropylacetanilide.

9. A method of controlling undesirable vegetation which comprises the application of said vegetation of a herbicidal composition comprising
    (a) a herbicidally effective amount of 2-(2-chloro-4-methanesulfonylbenzoyl)-1,3-cyclohexanedione;
    (b) a herbicidally effective amount of a compound selected from the group consisting of 2-chloro-4-(ethylamino)-6-(isopropylamino)-s-triazine, 3-amino-2,5-dichlorobenzoic acid, and 2-chloro-N-isopropylacetanilide, and mixtures thereof,
    at a weight ratio of (a) to (b) of from about 1:2 to about 2:1.

10. The method of claim 9 wherein (b) is 2-chloro-4-(ethylamino)-6-(isopropylamino)-s-triazine.

11. The method of claim 9 wherein (b) is 3-amino-2,5-dichlorobenzoic acid.

12. The method of claim 9 wherein (b) is 2-chloro-N-isopropylacetanilide.

* * * * *